(12) United States Patent
Chien

(10) Patent No.: US 8,851,074 B2
(45) Date of Patent: Oct. 7, 2014

(54) BREATHING MASK

(75) Inventor: Chih-Tsan Chien, New Taipei (TW)

(73) Assignee: Apex Medical Corp., New Taipei (TW)

( * ) Notice: Subject to any disclaimer, the term of this patent is extended or adjusted under 35 U.S.C. 154(b) by 429 days.

(21) Appl. No.: 13/354,815

(22) Filed: Jan. 20, 2012

(65) Prior Publication Data

US 2013/0186404 A1    Jul. 25, 2013

(51) Int. Cl.
*A61M 16/06* (2006.01)
*A61M 16/08* (2006.01)

(52) U.S. Cl.
USPC ............ 128/206.27; 128/206.21; 128/202.27; 128/200.24

(58) Field of Classification Search
USPC ............ 128/200.24, 200.26, 202.27, 204.18, 128/204.21, 205.25, 206.21, 206.24, 128/206.27, 207.11, 207.13, 207.18
See application file for complete search history.

(56) References Cited

U.S. PATENT DOCUMENTS

| | | | | |
|---|---|---|---|---|
| 8,424,528 | B2 * | 4/2013 | Eifler et al. .............. | 128/206.27 |
| 8,636,007 | B2 * | 1/2014 | Rummery et al. ........ | 128/207.13 |
| 2003/0196658 | A1 * | 10/2003 | Ging et al. ............... | 128/201.22 |
| 2003/0200970 | A1 * | 10/2003 | Stenzler et al. .......... | 128/207.18 |
| 2005/0011524 | A1 * | 1/2005 | Thomlinson et al. .... | 128/207.18 |
| 2012/0138061 | A1 * | 6/2012 | Dravitzki et al. ........ | 128/205.25 |

* cited by examiner

*Primary Examiner* — Annette Dixon
(74) *Attorney, Agent, or Firm* — C. G. Mersereau; Nikolai & Mersereau, P.A.

(57) ABSTRACT

A breathing mask has a mask body, a mounting bracket and a universal connecting tube. The mask body has a first universal socket bracket having a first spherical recess. The mounting bracket is mounted on the mask body and has a second universal socket bracket having a second spherical recess. The universal connecting tube is mounted universally pivotally in the mask body and has a ball joint mounted universally rotatably in the first and second spherical recesses. The universally rotating ball joint allows a breathing tube connected to the universal connecting tube to pivot to any orientations and prevents the breathing tube from over bending.

11 Claims, 11 Drawing Sheets

BREATHING MASK

BACKGROUND OF THE INVENTION

1. Field of the Invention

The present invention relates to a mask, and more particularly to a breathing mask that is connected to a breathing tube and allows the breathing tube to rotate universally such that the breathing tube is able to pivot to a proper orientation preventing itself from over bending and obstructing the air or oxygen conveyance and even pulling the mask to result in leakage no matter what position a patient is located relative to a breathing apparatus.

2. Description of Related Art

A breathing mask is worn on a patient's head and allows the patient to connect to a breathing apparatus and breathe through the breathing apparatus. A conventional breathing mask has a mask body and a headband. The mask body is mounted adjacent to the patient's nose and has two nostril tubes mounted on the mask body and press-contacting and slightly extending into the patient's nostrils. Furthermore, the mask body is able to engage a breathing tube that is connected to a breathing apparatus such that the oxygen is conveyed into the patient's nasal cavity. The headband is attached to the patient's head to ensure that the mask body is fastened securely on the patient's nose.

However, the mask body mounted on the breathing tube by a general mounting manner does not allow the breathing tube to rotate relative to the mask body. When a relative position of the patient to the breathing apparatus is changed, the breathing tube bends in different directions. An excessive bending extent of the breathing tube narrows an internal passage thereof and negatively affects the oxygen conveyance therein. The over bent breathing tube even inadvertently separates from the breathing apparatus or mask body and leads to interrupt the related therapy or endanger the patient's life.

To overcome the shortcomings, the present invention provides a breathing mask to mitigate or obviate the aforementioned problems.

SUMMARY OF THE INVENTION

The main objective of the invention is to provide a breathing mask that is connected to a breathing tube and allows the breathing tube to rotate universally such that the breathing tube is able to pivot to a proper orientation preventing itself from over bending and obstructing the air or oxygen conveyance and even pulling the mask to result in leakage no matter what position a patient is located relative to a breathing apparatus.

A breathing mask in accordance with the present invention has a mask body, a mounting bracket and a universal connecting tube. The mask body has a first universal socket bracket having a first spherical recess. The mounting bracket is mounted on the mask body and has a second universal socket bracket having a second spherical recess. The universal connecting tube is mounted universally pivotally in the mask body and has a ball joint mounted universally rotatably in the first and second spherical recesses. The universally rotating ball joint allows a breathing tube connected to the universal connecting tube to pivot to any orientations and prevents the breathing tube from over bending.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
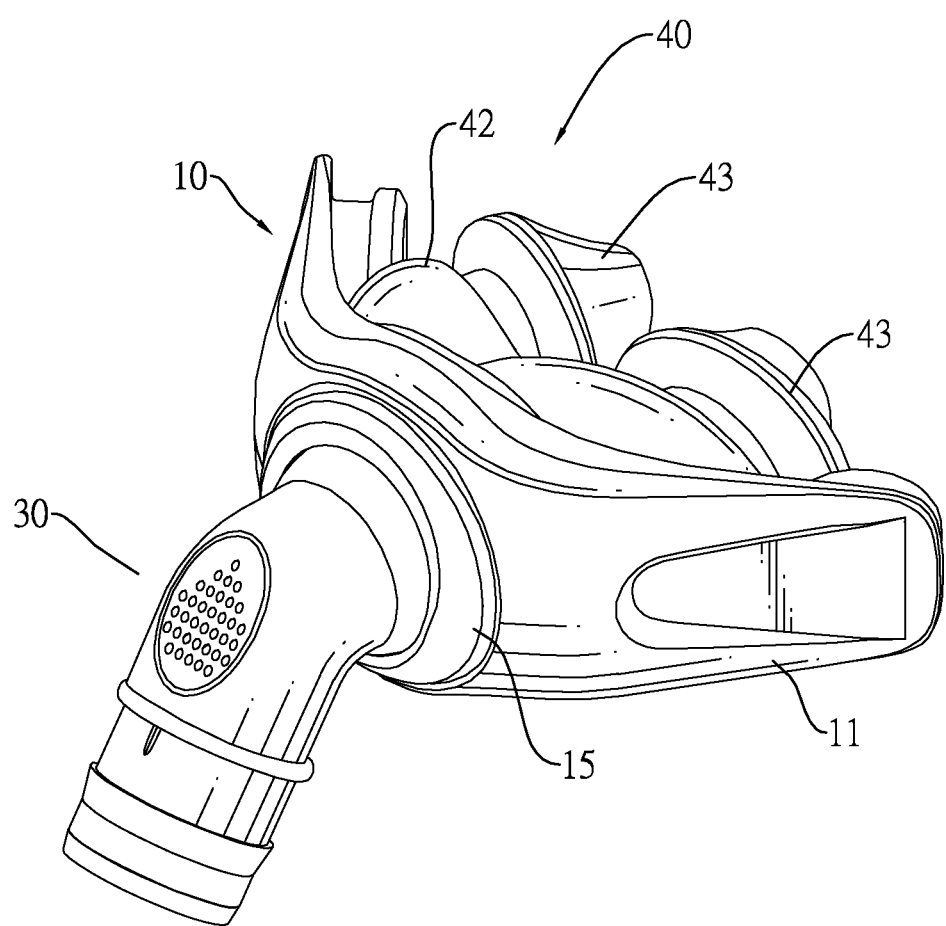
FIG. 1 is a perspective view of a breathing mask in accordance with the present invention.
Figure 2:
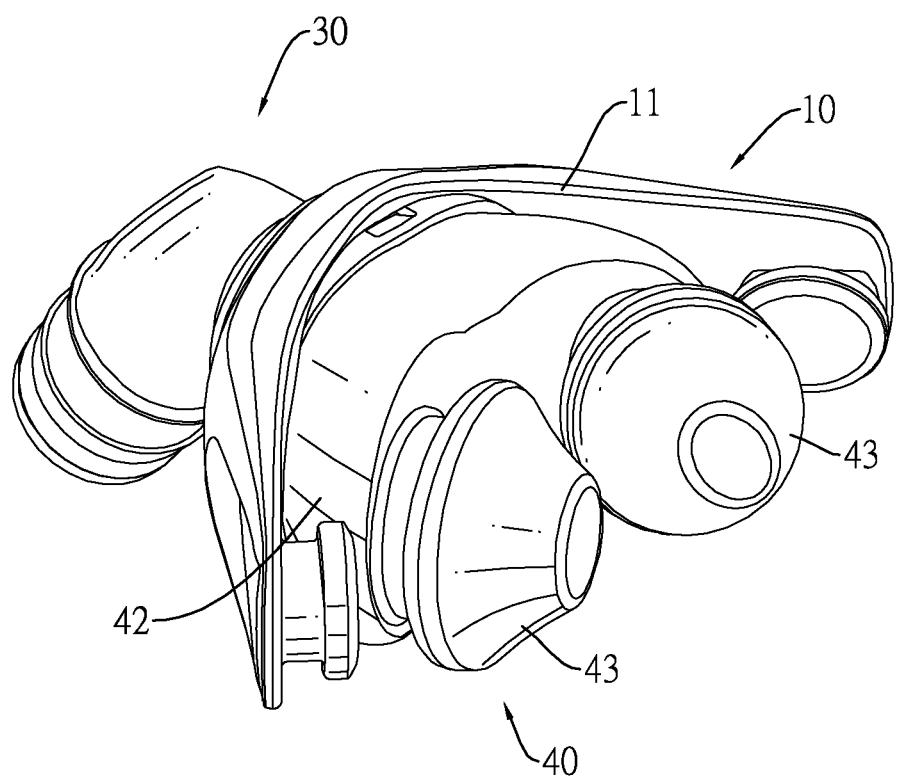
FIG. 2 is another perspective view of the breathing mask in FIG. 1.

With reference to FIGS. 1 to 3 and 10, a breathing mask 1 is connected to a breathing tube 97 and comprises a mask body 10, a mounting bracket 20, a universal connecting tube 30, a connection bracket 40, two side bands 90 and a rear band 95.

Figure 4:
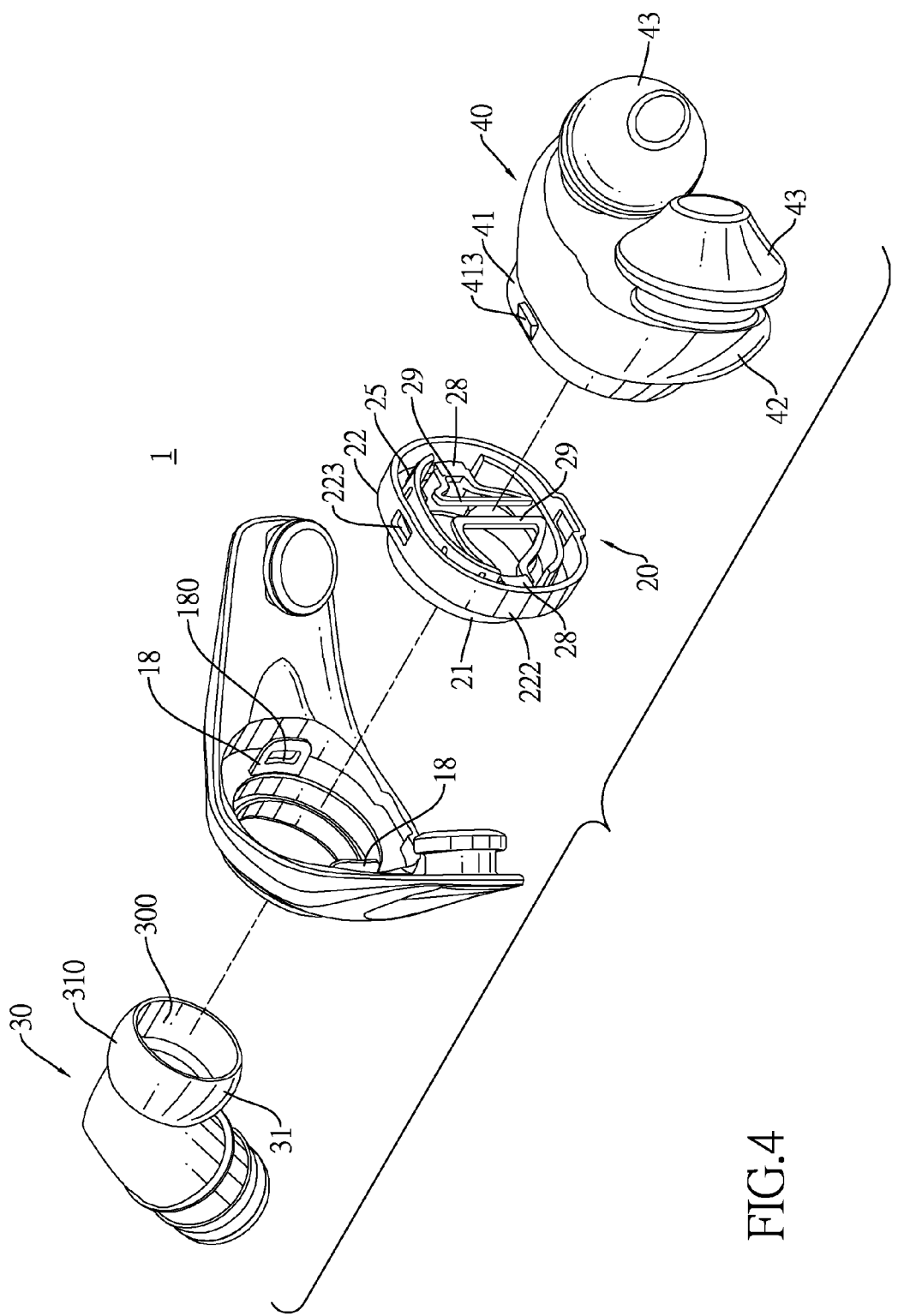
FIG. 4 is another exploded perspective view of the breathing mask in FIG. 3.

With further reference to FIG. 4, the mask body 10 has a frame 11 and a first universal socket bracket 15.

The frame 11 has two side ends and a through hole 12 defined through the frame 11.

Figure 5:
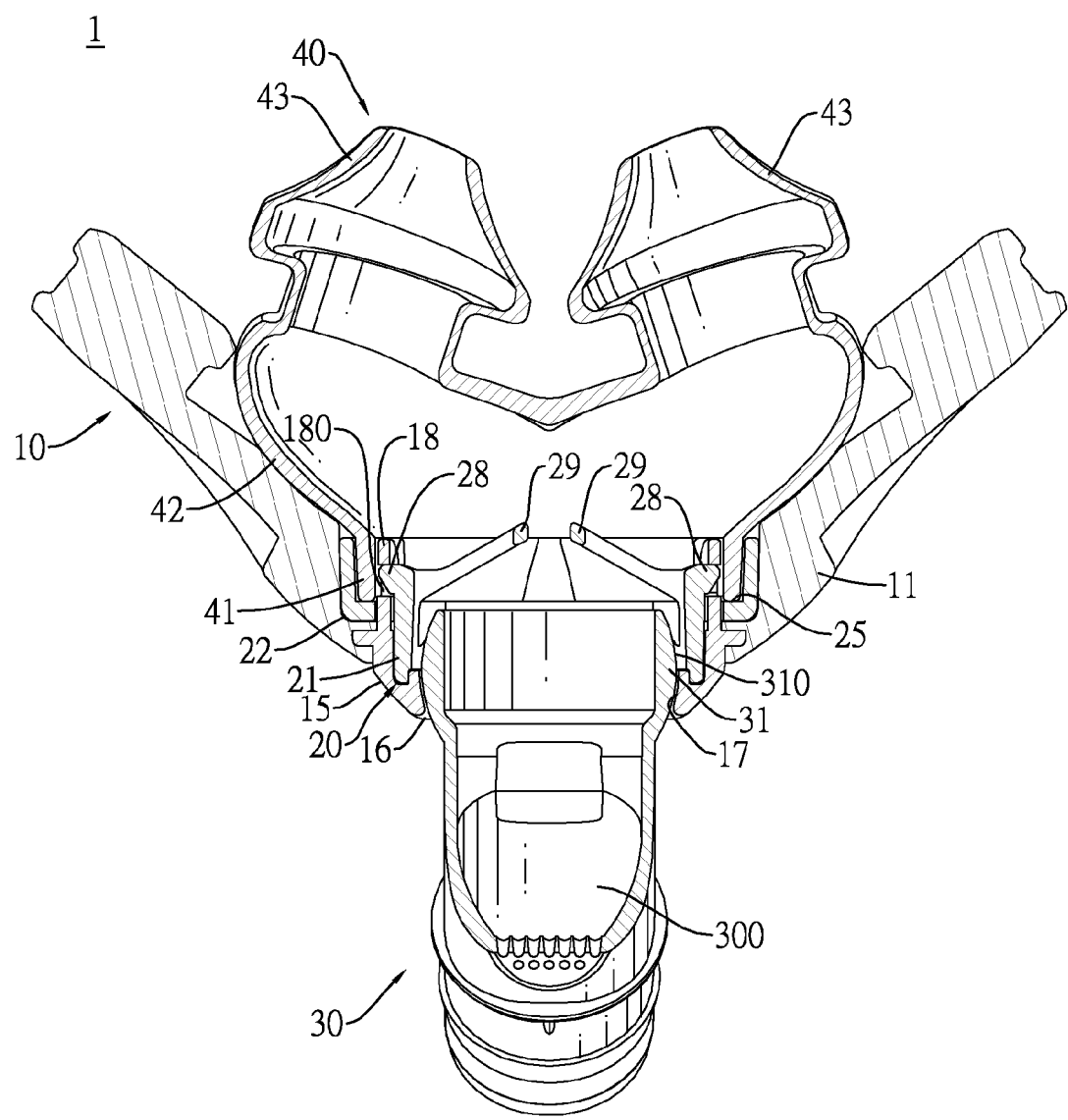
FIG. 5 is a cross sectional top view of the breathing mask in FIG. 1.
Figure 6:
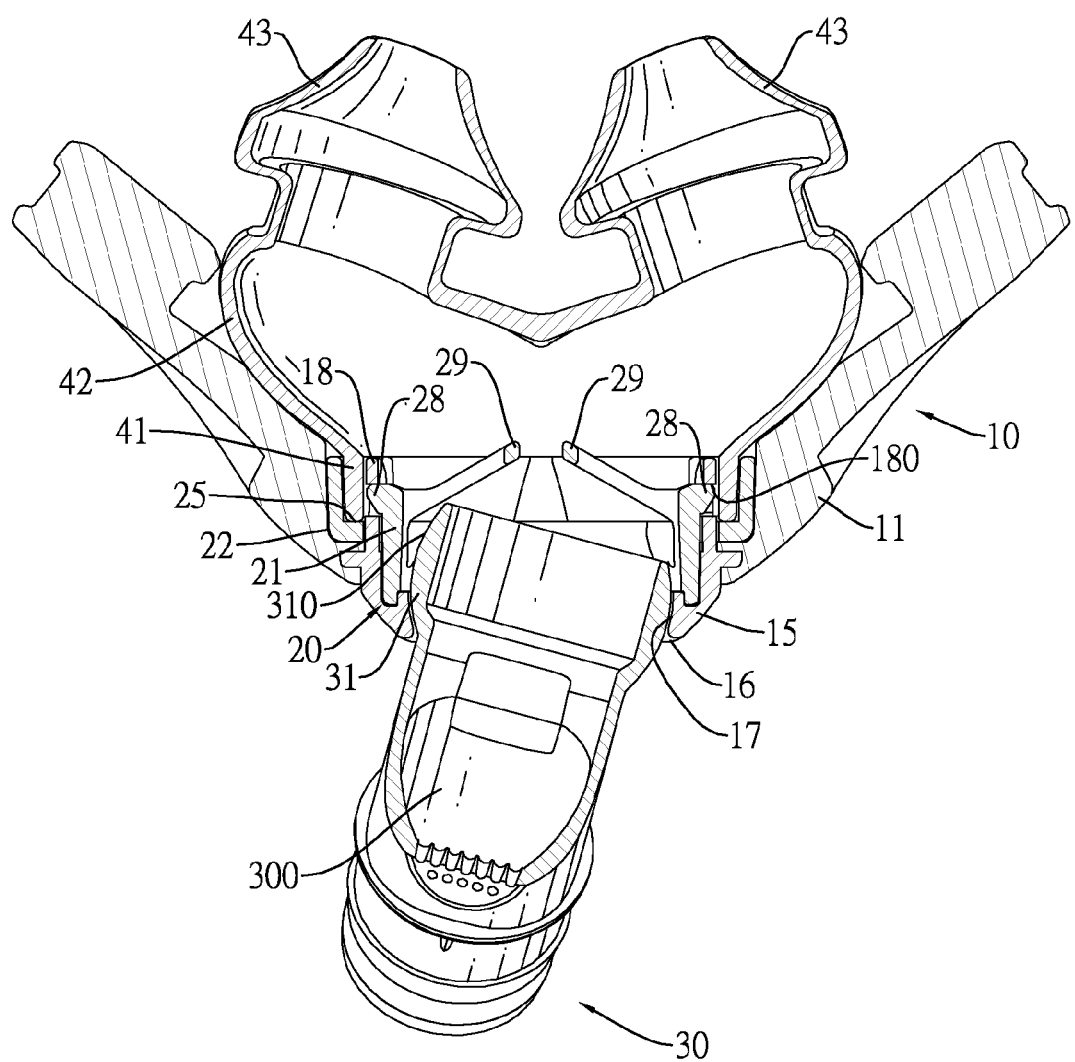
FIG. 6 is an operational cross sectional top view of the breathing mask in FIG. 5.

With further reference to FIGS. 5 and 6, the first universal socket bracket 15 is mounted securely in the through hole 12 and has a rear end, a mounting hole 16 and a first spherical recess 17. The mounting hole 16 is defined through the first universal socket bracket 15 and has an inner surface. The first spherical recess 17 is annular and is defined in the inner surface of the mounting hole 16.

Figure 7:
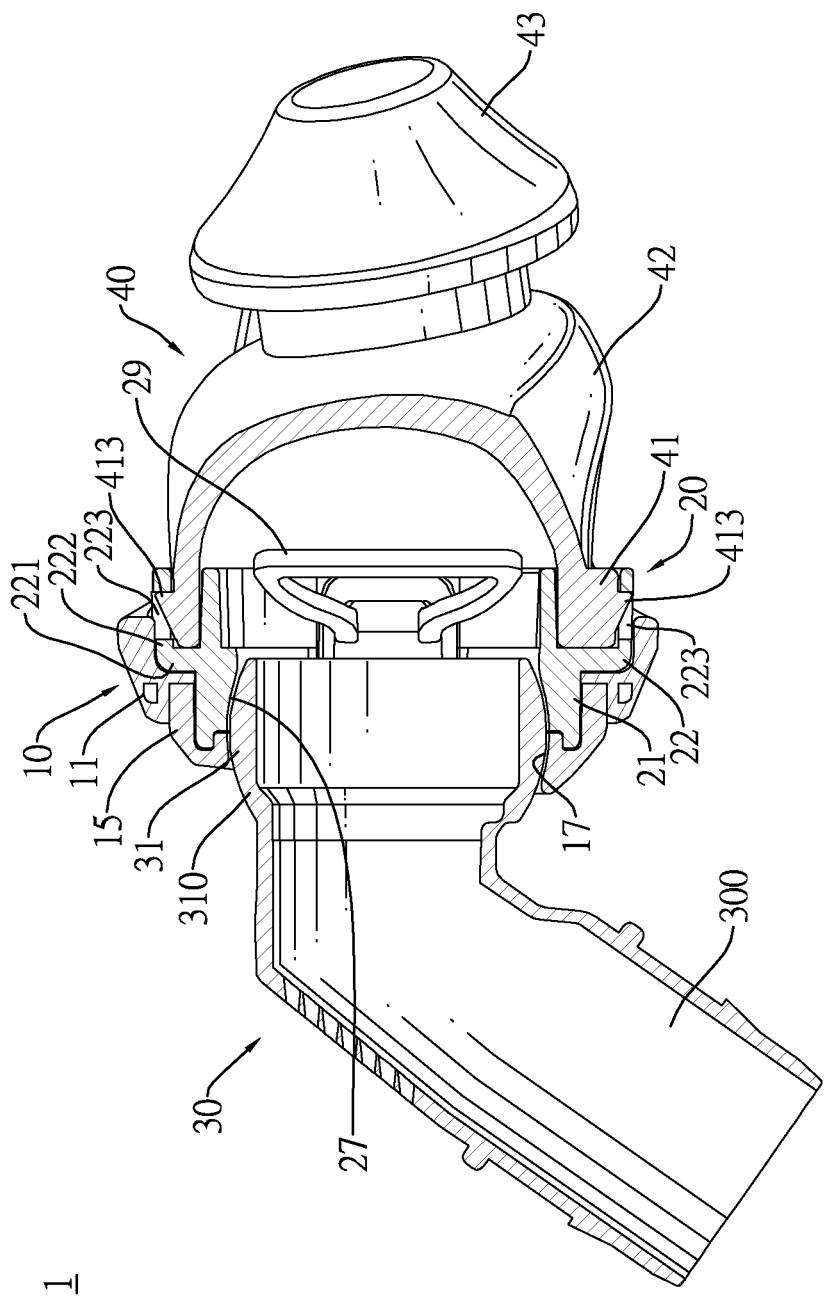
FIG. 7 is a cross sectional side view of the breathing mask in FIG. 1.
Figure 8:
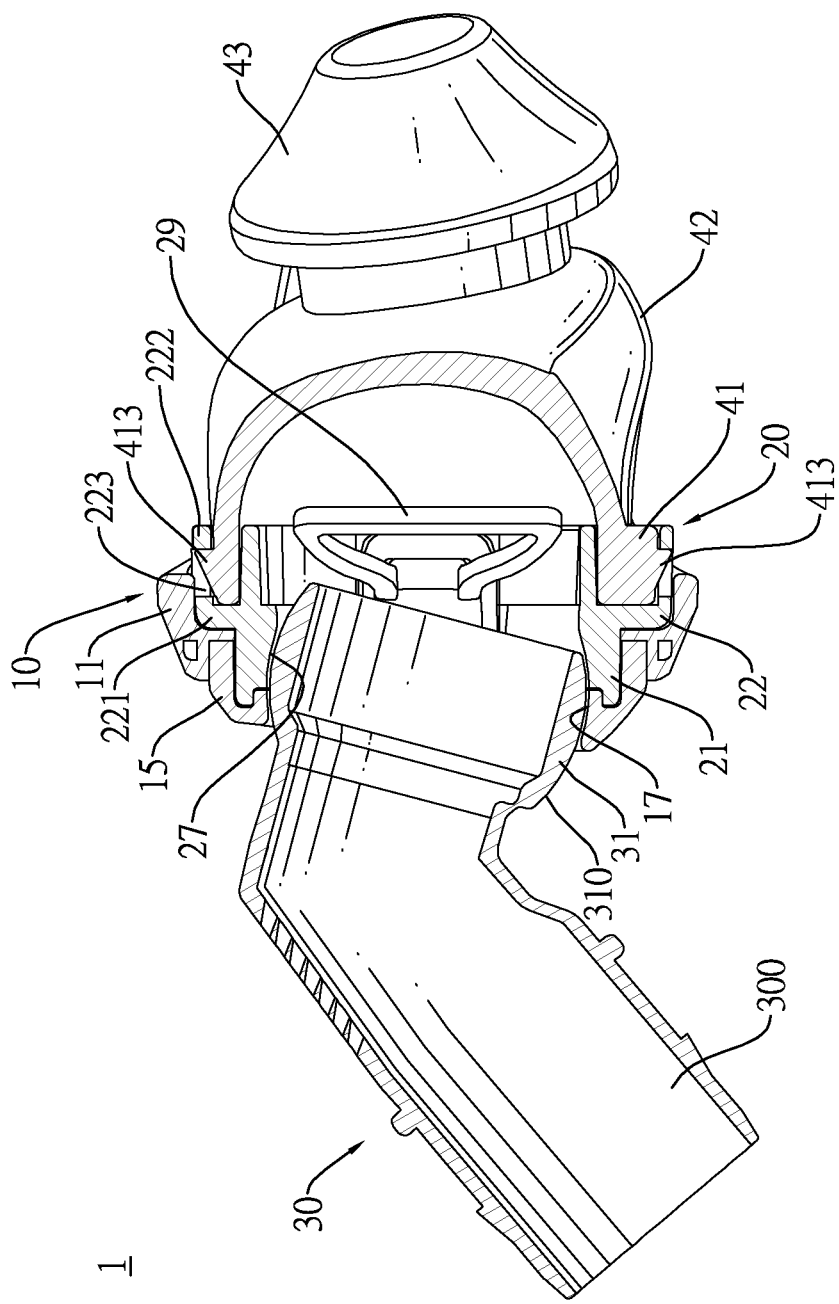
FIG. 8 is an operational cross sectional side view of the breathing mask in FIG. 7.

With further reference to FIGS. 7 and 8, the mounting bracket 20 is mounted securely on the mask body 10 and has a second universal socket bracket 21 and an assembling member 22.

The second universal socket bracket 21 is hollow and tubular and has a rear end, a fastening hole 26 and a second spherical recess 27. The fastening hole 26 is defined through the second universal socket bracket 21 and has an inner surface. The second spherical recess 27 is annular, is defined in the inner surface of the fastening hole 26 and combines the first spherical recess 17 to form a universal socket.

The assembling member 22 is formed on and protrudes backward from the second universal socket bracket 21.

The universal connecting tube 30 is mounted universally pivotally in the mask body 10 and the mounting bracket 20, protrudes forward from the mask body 10 and has a front end, a rear end, a channel 300 and a ball joint 31. The channel 300 is defined through the universal connecting tube 30. The ball joint 31 is formed on the rear end of the universal connecting tube 30, is mounted universally rotatably in the universal socket formed from the first and second spherical recesses 17, 27 for 360 degrees rotation and has an outer surface 310. The outer surface 310 of the ball joint 31 is spherical so as to smoothly contact and rotate relative to the first and second spherical recesses 17, 27. The ball joint 31 is capable of fluently rotating for 360 degrees due to the limitation made by the first and second spherical recesses 17, 27 instead of being displaced. Furthermore, the universal connecting tube 30 may he made of resilient material such as plastic or rubber such that the universal connecting tube 30 may be press-fitted into or detached from the universal socket from the combined first and second spherical recesses 17, 27 through the front of the mask body 10. Therefore, the universal connecting tube 30 may be quickly attached to or detached from the front of the mask body 10. Alternatively, the aforementioned components are fabricated according to a different step order of assembling the universal connecting tube 30 on the mask body 10 and then combining the mounting bracket 20 to the mask body 10.

The connection bracket 40 is mounted on the assembling member 22 of the mounting bracket 20 opposite to the mask body 10 and may be inserted into a patient's nostrils.

Figure 9:
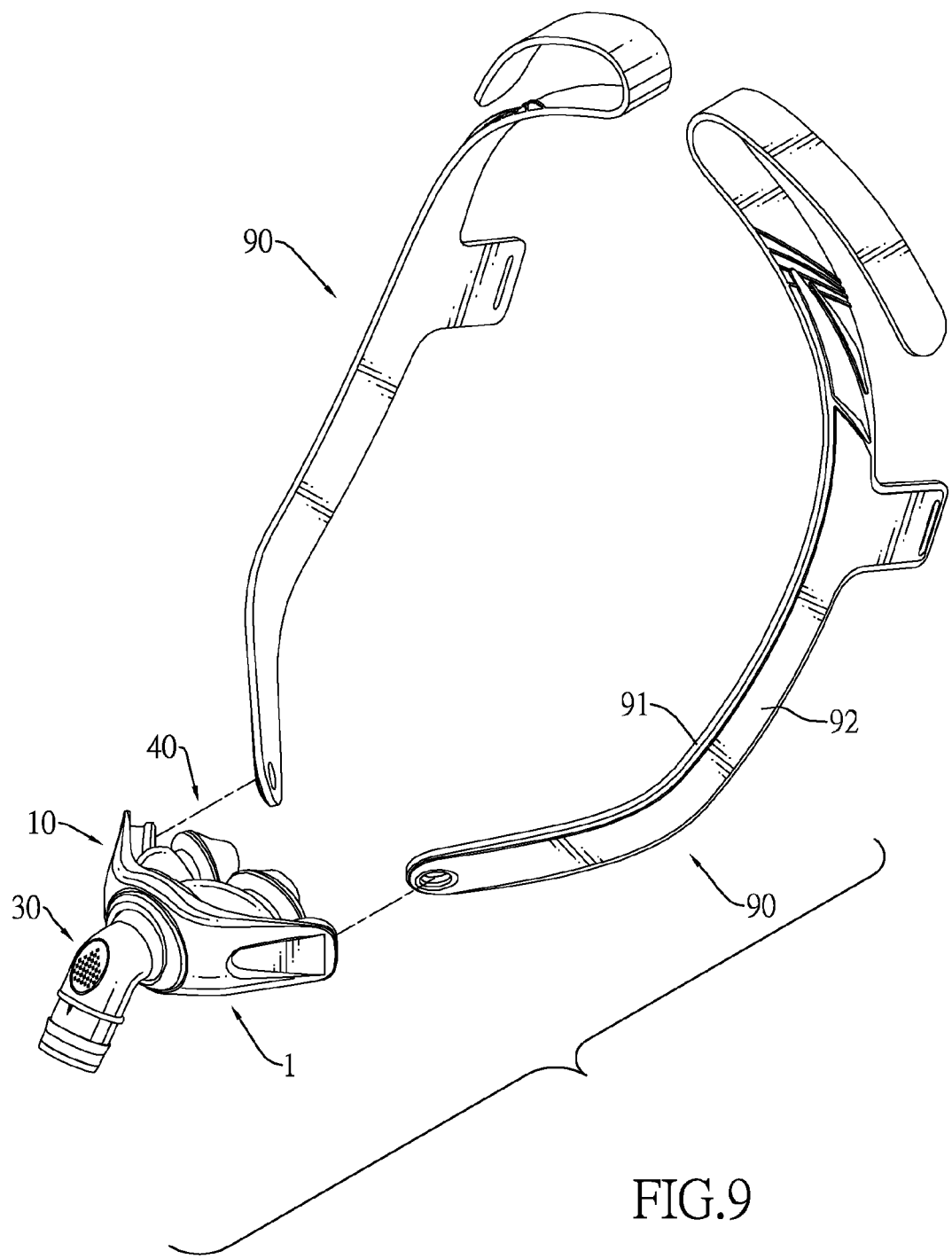
FIG. 9 is an exploded perspective view of the breathing mask in FIG. 1 with two side bands.
Figure 10:
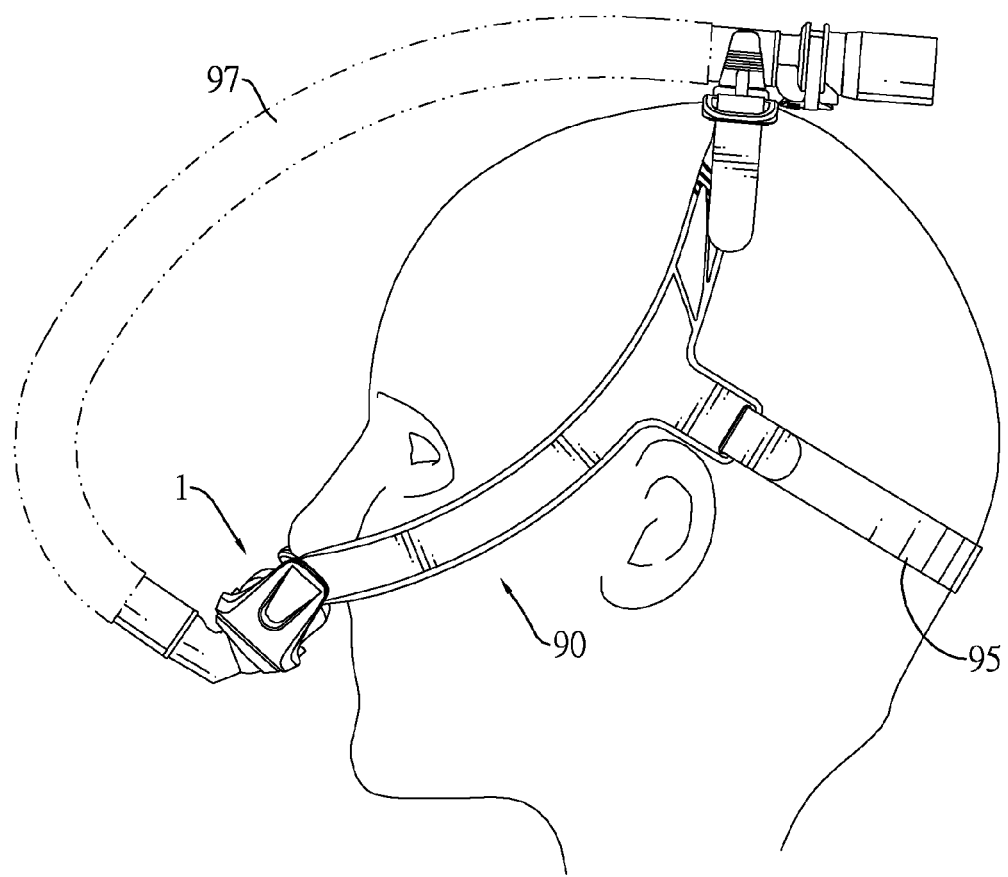
FIG. 10 is an operational side view of the breathing mask in FIG. 9 worn on a human head.
Figure 11:
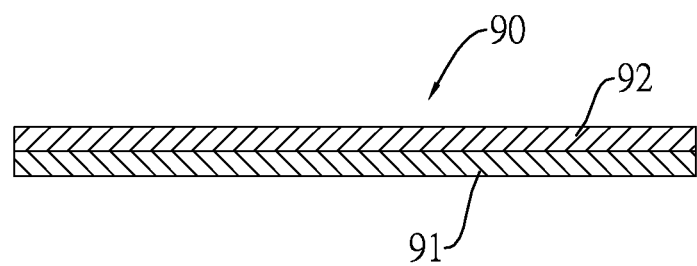
FIG. 11 is a cross sectional view of a side band of the breathing mask in FIG. 9.

With further reference to FIGS. 9 and 11, the side bands 90 are connected pivotally and respectively to side ends of the frame 11. Each side band 90 is a dual-layer structure and has a fabric layer 91 and a glue layer 92. The glue layer 92 may be a polyester polyurethane layer 92 and is formed on the fabric layer 91 by hot-pressing processes. The fabric layer 91 is soft and makes the user feel comfortable when the side bands are fastened on the user's head. The polyester polyurethane layer 92 has excellent flexibility and supportive strength to allow the side band 90 to intimately fit the patient's face and provide comfort.

The rear band 95 is attached between the side bands 90.

In a preferred embodiment of the present invention, with further reference to FIG. 4, the mask body 10 has multiple buckling members 18 formed on and protruding backward from the rear end of the first universal socket bracket 15. Each buckling member 18 has a buckling hole 180 defined through the buckling member 18. The mounting bracket 20 has multiple hooks 28 and multiple releasing pulls 29. The hooks 28 may be resilient. The hooks 28 are formed on and protrude back from the rear end of the second universal socket bracket 21, correspond to the buckling members 18 and detachably hook respectively in the buckling holes 180 of the buckling members 18. The releasing pulls 29 are U-shaped, formed on the rear end of the second universal socket bracket 21, and correspond to the hooks 28. Each releasing pull 29 has two ends connected to one of the hooks 28 such that the releasing pull 29 and the hook 28 cooperatively form a ring-shaped configuration. Furthermore, each releasing pull 29 extends transversely inward and is inclined backward. Pulling the releasing pulls 29 by fingers disengages the hooks 28 from the buckling holes 180 of the buckling members 18. Therefore, the mounting bracket 20 may be quickly attached to or detached from the mask body 10 for quick assembly and disassembly purposes.

Figure 3:
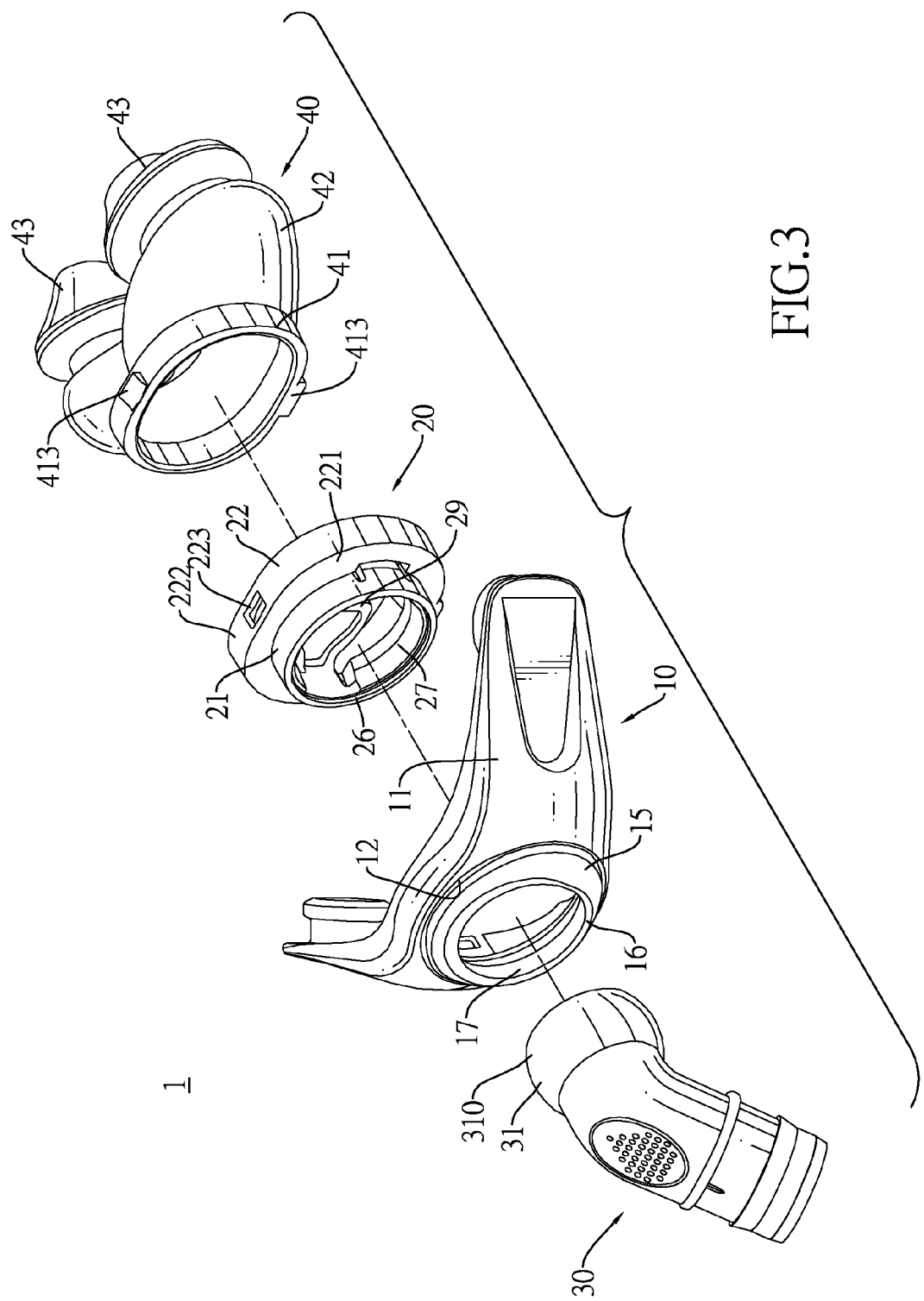
FIG. 3 is an exploded perspective view of the breathing mask in FIG. 1.

In a preferred embodiment of the present invention, with further reference to FIGS. 3 and 4, the assembling member 22 of the mounting bracket 20 is annular and has a radial flange 221, an axial flange 222 and an annular assembling slot 25. The radial flange 221 is formed on and protrudes radially outward from the second universal socket bracket 21. The axial flange 222 is formed on and protrudes axially backward from the radial flange 221. The annular assembling slot 25 is defined between the axial flange 222 and an outer surface of the second universal socket bracket 21. The connection bracket 40 has a hollow sleeve 41, a hollow body 42 and two hollow nostril insertions 43. The sleeve 41 is mounted detachably in the annular assembling slot 25 of the assembling member 22 and has a rear end. The body 42 is formed on the rear end of the sleeve 41 and communicates with the sleeve 41 and has a rear end. The nostril insertions 43 are formed on the rear end of the body 42 and communicate with the body 42 and each nostril insertion 43 has an air outlet hole defined through the nostril insertion 43.

In a preferred embodiment of the present invention, the mounting bracket 20 has multiple assembling holes 223 defined in the axial flange 222 of the assembling member 22. The connection bracket 40 has multiple assembling hooks 413 formed on an outer surface of the sleeve 41 and mounted detachably and respectively in the assembling holes 223 of the mounting bracket 20.

The present invention has the following advantages.

1. The universal connecting tube 30 pivots agilely relative to the mask body 10 for 360 degrees through a combination of the universal socket formed from the first and second spherical recesses 17, 27 and the ball joint 31. When a patient wears the breathing mask 1 with the universal connecting tube 30 connected to the breathing tube 97 linked to a breathing apparatus, the universal connecting tube 30 is capable of pivoting to an orientation allowing the breathing tube 97 to extend smoothly to prevent the breathing tube 97 from excessively bending and lowering the fluency of the air conveyance therein no matter what the patient's position is relative to the breathing apparatus.

2. The mounting bracket 20 is quickly attached to or detached from the mask body 10 through the buckling holes 180 of the buckling members 18 and the releasing pulls 29 for quick assembly and disassembly purposes.

3. The fabric layer 91 of the side band 90 is soft and makes the user feel comfortable when the side bands are fastened on the user's head. The polyester polyurethane layer 92 has excellent flexibility and supportive strength to allow the side band 90 to intimately fit the patient's face and provide comfort.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:
1. A breathing mask comprising:
  a mask body having
    a frame having two side ends and a through hole defined through the frame; and
    a first universal socket bracket mounted securely in the through hole and having
      a rear end;
      a mounting hole defined through the first universal socket bracket and having an inner surface; and
      a first spherical recess being annular and defined in the inner surface of the mounting hole;
  a mounting bracket mounted securely on the mask body and having
    a second universal socket bracket being hollow and tubular and having
      a rear end;
      a fastening hole defined through the second universal socket bracket and having an inner surface; and a second spherical recess being annular, defined in the inner surface of the second universal socket bracket and located adjacent to the first spherical recess; and an assembling member formed on and protruding backward from the second universal socket bracket;

a universal connecting tube mounted universally pivotally in the mask body and the mounting bracket, protruding forward from the mask body and having
a front end;
a rear end; and
a ball joint formed on the rear end of the universal connecting tube, mounted universally rotatably in the first and second spherical recesses; and a connection bracket mounted on the assembling member of the mounting bracket opposite to the mask body.

2. The breathing mask as claimed in claim 1, wherein the mask body has multiple buckling members formed on and protruding backward from the rear end of the first universal socket bracket, each buckling member having a buckling hole defined through the buckling member; and the mounting bracket has multiple hooks being resilient, formed on and protruding back from the rear end of the second universal socket bracket, corresponding to the buckling members and detachably hooking respectively in the buckling holes of the buckling members.

3. The breathing mask as claimed in claim 2, wherein the mounting bracket has multiple releasing pulls formed on the rear end of the second universal socket bracket and corresponding to the hooks; pulling the releasing pulls disengages the hooks from the buckling holes of the buckling members.

4. The breathing mask as claimed in claim 3, wherein each releasing pull is U-shaped and has two ends connected to one of the hooks such that the releasing pull and the hook cooperatively form a ring-shaped configuration; each releasing pull extends transversely inward and is inclined backward.

5. The breathing mask as claimed in claim 4, wherein the assembling member of the mounting bracket is annular and has a radial flange formed on and protruding radially outward from the second universal socket bracket;

an axial flange formed on and protruding axially backward from the radial flange; and an annular assembling slot defined between the axial flange and an outer surface of the second universal socket bracket.

6. The breathing mask as claimed in claim 5, wherein the connection bracket has a hollow sleeve mounted detachably in the annular assembling slot of the assembling member and having a rear end;

a hollow body formed on the rear end of the sleeve and communicating with the sleeve and having a rear end; and two hollow nostril insertions formed on the rear end of the body and communicating with the body and each nostril insertion having an air outlet hole defined through the nostril insertion.

7. The breathing mask as claimed in claim 6, wherein the mounting bracket has multiple assembling holes defined in the axial flange of the assembling member; and the connection bracket has multiple assembling hooks formed on an outer surface of the sleeve and mounted detachably and respectively in the assembling holes of the mounting bracket.

8. The breathing mask as claimed in claim 7, wherein the ball joint is prevented from being displaced due to limitation by the first and second spherical recesses.

9. The breathing mask as claimed in claim 8 further comprising
two side bands connected pivotally and respectively to side ends of the frame: and
a rear band attached between the side bands.

10. The breathing mask as claimed in claim 9, wherein each side band is a dual-layer structure and has a fabric layer and a glue layer formed on the fabric layer by hot-pressing processes.

11. The breathing mask as claimed in claim 10, wherein the glue layer is a polyester polyurethane layer.

* * * * *